United States Patent
Chastain et al.

(10) Patent No.: US 7,612,291 B2
(45) Date of Patent: Nov. 3, 2009

(54) COMPOSITE WIRE FOR IMPLANTABLE CARDIAC LEAD CONDUCTOR CABLE AND COILS

(75) Inventors: Stuart R. Chastain, Shoreview, MN (US); Russell L. Hoeker, Maple Grove, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/558,147

(22) Filed: Nov. 9, 2006

(65) Prior Publication Data

US 2007/0154729 A1 Jul. 5, 2007

Related U.S. Application Data

(60) Provisional application No. 60/735,296, filed on Nov. 10, 2005.

(51) Int. Cl.
*H01B 5/19* (2006.01)
(52) U.S. Cl. .................................. 174/126.1
(58) Field of Classification Search .......... 174/126.1, 174/126.2, 128.1, 128.2
See application file for complete search history.

(56) References Cited

U.S. PATENT DOCUMENTS

| | | | | |
|---|---|---|---|---|
| 2,417,459 A | * | 3/1947 | Eitel et al. ................. 313/354 |
| 3,864,807 A | * | 2/1975 | Schneider et al. ........... 148/530 |
| 4,078,299 A | * | 3/1978 | Furuto et al. ................ 29/599 |
| 4,112,905 A | * | 9/1978 | Stockel et al. ........ 123/169 EL |
| 4,127,700 A | * | 11/1978 | Stockel et al. .............. 428/558 |
| 4,860,446 A | | 8/1989 | Lessar et al. |
| 4,988,833 A | | 1/1991 | Lai |
| 5,097,100 A | * | 3/1992 | Jackson .................... 174/94 R |
| 5,182,785 A | | 1/1993 | Savegh et al. |
| 5,246,014 A | | 9/1993 | Williams et al. |
| 5,303,704 A | | 4/1994 | Molacek et al. |
| 5,330,521 A | | 7/1994 | Cohen |
| 5,358,517 A | | 10/1994 | Pohndorf et al. |
| 5,360,442 A | * | 11/1994 | Dahl et al. .................. 607/129 |
| 5,366,493 A | | 11/1994 | Scheiner et al. |
| 5,483,022 A | * | 1/1996 | Mar ....................... 174/128.1 |
| 5,584,873 A | | 12/1996 | Shoberg et al. |
| 5,630,840 A | * | 5/1997 | Mayer ...................... 623/66.1 |
| 5,676,694 A | | 10/1997 | Boser et al. |
| 5,760,341 A | | 6/1998 | Laske et al. |
| 5,845,396 A | | 12/1998 | Altman et al. |
| 6,099,457 A | * | 8/2000 | Good ............................ 600/8 |
| 6,104,961 A | | 8/2000 | Conger et al. |
| 6,477,429 B1 | | 11/2002 | Conger et al. |
| 7,280,875 B1 | * | 10/2007 | Chitre et al. ................ 607/122 |
| 7,340,305 B2 | * | 3/2008 | Fischbach et al. ............ 607/36 |
| 2005/0027338 A1 | * | 2/2005 | Hill ............................. 607/116 |
| 2006/0074470 A1 | * | 4/2006 | Bartels et al. ............... 607/119 |

FOREIGN PATENT DOCUMENTS

JP 05-126321 * 5/1993

* cited by examiner

*Primary Examiner*—Chau N Nguyen
(74) *Attorney, Agent, or Firm*—Schwegman, Lundberg & Woessner, P.A.

(57) ABSTRACT

A composite wire can include a core including a material chosen from the group consisting of Ag and Ir and combinations thereof, a shell around the core including a material chosen from the group consisting of Ta, MP35N, and Nb and combinations thereof, and an outer layer over the shell including a material chosen from the group consisting of Pt and Pt—Ir and combinations thereof.

22 Claims, 3 Drawing Sheets

US 7,612,291 B2

COMPOSITE WIRE FOR IMPLANTABLE CARDIAC LEAD CONDUCTOR CABLE AND COILS

CROSS-REFERENCE TO RELATED APPLICATION

This application claims the benefit under 35 U.S.C. 119 (e) of U.S. Provisional Application No. 60/735,296, filed on Nov. 10, 2005, which is hereby incorporated by reference in its entirety.

FIELD OF THE INVENTION

This invention relates to the field of medical leads, and more specifically to a composite wire for a lead.

BACKGROUND

Leads implanted in or about the heart have been used to reverse certain life threatening arrhythmia, or to stimulate contraction of the heart. Electrical energy is applied to the heart via electrodes on the leads to return the heart to normal rhythm.

Materials chosen for lead conductors can have varying properties, with some being more corrosion resistant, some being stronger, some having better electrical properties, and so on. Design of new types of leads is facilitated by conductors having better overall properties.

DETAILED DESCRIPTION

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the present invention is defined by the appended claims and their equivalents.

Figure 1:
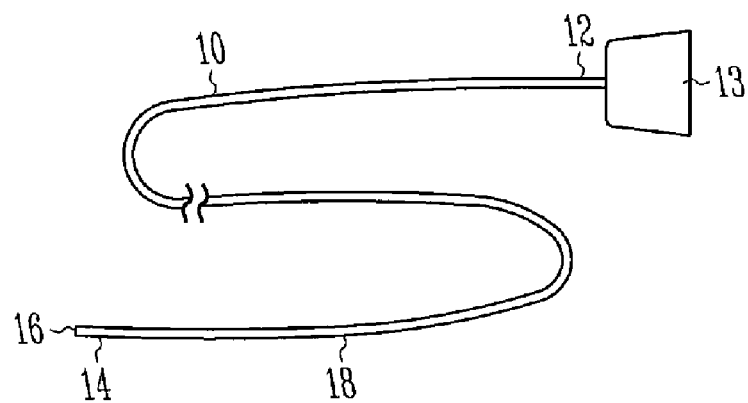
FIG. 1 shows a lead and pulse generator according to at least one embodiment.

FIG. 1 shows a lead 10, in accordance with one embodiment. Lead 10 is an implantable lead having a proximal end 12 connectable to an energy source, such as a pulse generator 13, and a distal end 14 having one or more electrode(s) 16. Lead 10 includes one or more conductors extending from pulse generator 13 to electrode(s) 16. Biocompatible outer insulation 18 covers the conductors. The lead system can be unipolar, bipolar, or multi-polar.

The electrode(s) 16 can include a tip electrode, a ring electrode, a coil electrode, and combinations of such electrodes. In some examples, the pulse generator 13 housing can be an electrode. In some embodiments, lead 10 can be configured to allow both a stylet or catheter delivery. For example, an opening can be left through the middle of the lead to allow either a stylet or a guidewire to be used. In other embodiments, lead 10 can be delivered as either an epicardial lead or a subcutaneous lead.

Pulse generator 13 can be implanted in a surgically-formed pocket in a patient's chest or other desired location. Pulse generator 13 generally includes electronic components to perform signal analysis and processing, and control. Pulse generator 13 can include a power supply such as a battery, a capacitor, and other components housed in a case. The device can include microprocessors to provide processing, evaluation, and to determine and deliver electrical shocks and pulses of different energy levels and timing for defibrillation, cardioversion, CHF therapy, and pacing to a heart via lectrode(s) 16 in response to cardiac arrhythmia including fibrillation, tachycardia, and bradycardia.

Figure 2:
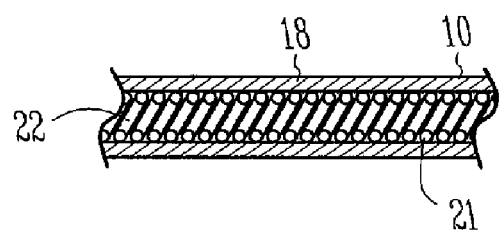
FIG. 2 shows a side cross-section of the lead of FIG. 1.

FIG. 2 shows a cross section of a portion of lead 10, in accordance with one embodiment. Lead 10 includes outer insulation 18, which can be polyurethane for example. One or more coiled conductors 21 are positioned within outer insulation 18 and define a lumen 22. Conductor 21 can be a single wire, or a multi-filar wire coil. Some embodiments use two or more conductors in a coaxial configuration in which the conductors are electrically insulated from each other. Referring also to FIG. 1, conductor 21 conducts electrical signals and pulses between electrode 16 and pulse generator 13. Conductor 21 has one end electrically and mechanically coupled to electrode 16 and another end electrically and mechanically coupled to a terminal on the proximal end of lead 10 that is then plugged into pulse generator 13.

Design considerations need to be taken into consideration when choosing the material(s) for conductor 21 so a robust mechanical and electrical connection can be made between the conductor and the electrode 16 and the lead terminal, for example. Also, the electrical properties of the conductor 21 need to be considered to provide proper operation of the pulse generator system. Other factors in choosing proper conductor materials include the fatigue resistance of the conductor and the corrosion resistance of the conductor, for example.

Figure 3:
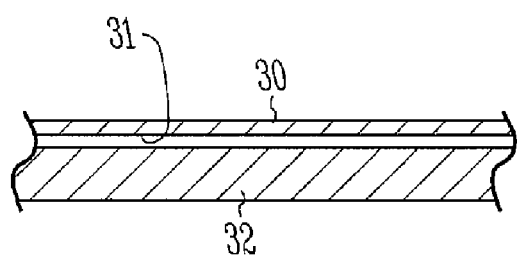
FIG. 3 shows a side cross-section of a lead according to at least one embodiment.

FIG. 3 shows a lead 30 having a conductor 31, in accordance with one embodiment. Conductor 31 uses a straight wire configuration instead of a coiled configuration. Conductor 31 can be a twisted strand composite or homogeneous cable, as will be discussed below. The conductor 31 can be surrounded by an outer insulation 32. As discussed above, certain considerations need to be taken in choosing the proper material(s) for conductor 31.

In various examples to be discussed below, the present system provides composite wire to make conductor cables for implantable leads. Some embodiments utilize two or more different materials for a composite wire so that the different materials can optimize their given properties.

Figure 4:
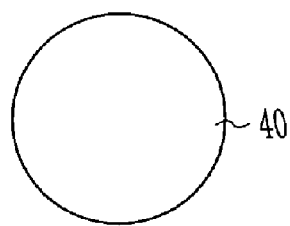
FIG. 4 shows a cross-section of a wire according to at least one embodiment.

For example, FIG. 4 shows a cross section of a conductor 40, in accordance with one embodiment. Conductor 40 can be used in various different configurations (to be discussed below with FIGS. 11-13). In one example, conductor 40 is a homogeneous wire formed of tantalum (Ta).

Figure 5:
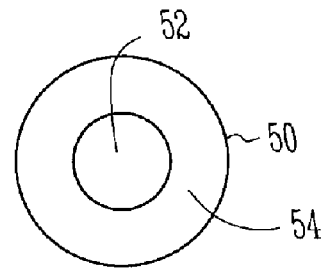
FIG. 5 shows a cross-section of a composite wire according to at least one embodiment.

FIG. 5 shows a bi-layer composite wire 50, in accordance with one embodiment. Composite wire 50 can be used in many different configurations, as will be discussed below. In one embodiment, composite wire 50 includes a core 52 including Ta, molybdenum (Mo), silver (Ag), Rhodium (Rh), gold (Au), titanium (Ti), copper (Cu), or iridium (Ir), or combinations thereof, and a shell 54 around core 52 including stainless steel, a cobalt alloy such as MP35N, Ta, niobium (Nb), platinum (Pt), or Pt—Ir, and combinations thereof.

In one embodiment, core 52 consists of Mo and shell 54 includes MP35N. In one embodiment, core 52 includes Ag, Au, or Mo, and the shell 54 includes Ta or Nb. In one embodiment, the core 52 includes Ir and the shell 54 includes Ta or Nb. In one embodiment, core 52 includes Mo and shell 54 includes Ta with the Mo core 52 being between about 10% to 50% by volume of the overall wire. In one embodiment, core 52 includes Ag and shell 54 includes Ta with the Ag core 52 being between about 5% to 25% by volume of the overall wire. In one embodiment, core 52 includes Au and shell 54 includes Ta with the Au core 52 being between about 5% to 50% by volume of the overall wire. In one embodiment, core 52 includes Cu and shell 54 includes Ta with the Cu core 52 being between about 5% to 25% by volume of the overall wire.

Different materials can be used for different needs as chosen by the lead designer. In one embodiment, wire 50 includes a core 52 including Mo and a shell 54 including MP35N, Ta, or Pt—Ir, or combinations thereof. In one example, wire 50 can have an overall diameter of about 0.0005 inches to about 0.010 inches. In some embodiments, the wire can be coiled into a multi-filar coil or twisted together with other composite wire strands into a multi-filament cable, such as discussed below for FIGS. 11-13.

Wire 50 can be formed by a cold-drawn process, such as a drawn-filled tube (DFT®) configuration, for example. (A company that can form DFT materials includes Fort Wayne Materials of Fort Wayne, Ind.). In some embodiments, the wire has an outer diameter of about 0.0008 inches to about 0.010 inches.

Figure 7:
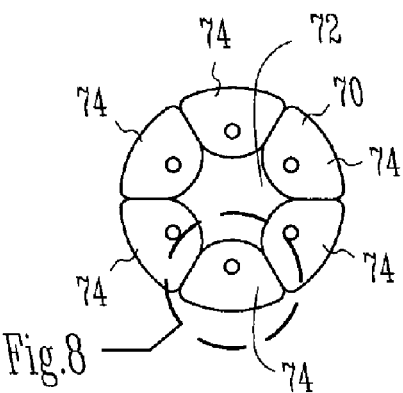
FIG. 7 shows a cross-section of a composite wire according to at least one embodiment.
Figure 9:
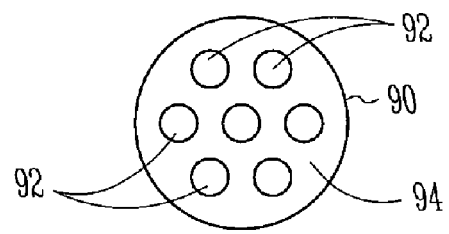
FIG. 9 shows a cross-section of a composite wire according to at least one embodiment.
Figure 10:
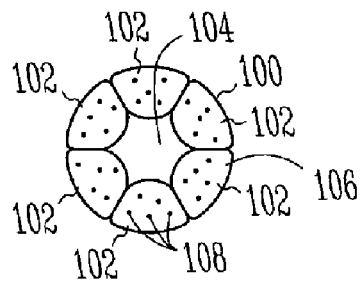
FIG. 10 shows a cross-section of a composite wire according to at least one embodiment.

As will be discussed below, in some embodiments, core 52 can include a composite structure, such as shown in FIG. 7, 9, or 10.

Figure 6:
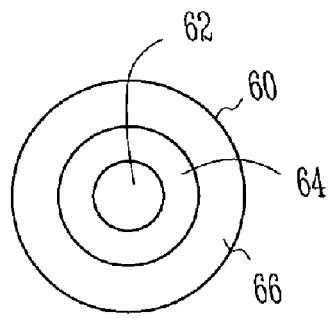
FIG. 6 shows a cross-section of a composite wire according to at least one embodiment.

FIG. 6 shows a tri-layer composite wire 60 according to one embodiment. Wire 60 includes a core 62, a shell or first layer 64 surrounding the core, and an outer layer 66 surrounding the first layer 64. In various embodiments, wire 60 can be formed by a cold-drawn process. In some examples, the composite wire is heat-treated. The outer layer 66 is provided to enhance the corrosion resistance and/or drawability of the wire. The core 62 is provided to reduce the electrical resistance and/or provide mechanical redundancy for the wire. In some examples, the outer layer 66 can be applied to the first layer 64 either before or after the final drawing operation by means of cladding, electroplating, or vapor deposition, for example. In some embodiments layer 66 can have a thickness of about 1.0 to 25.0 microns.

In various embodiments, wire 60 can have an outer diameter of about 0.0008 inches to about 0.010 inches.

In various embodiments, core 62 can include Ag, Au, Rh, Mo, alloy of Ta and Mo, Cu, Ir, or Ti, shell 64 can include stainless steel, Ta, MP35N, or Pt—Ir, and outer layer 66 can include Ag, Pt, Pt—Ir (5-30% Ir), Ta, Rh, Ti, or Nb.

In some embodiments, core 62 can include Ag, Au, Mo, or Ir, shell 64 can include Ta, MP35N, or Nb, and outer layer 66 can include Pt, Pt—Ir, MP35N, or stainless steel.

In some embodiments, core 62 can include Ag or Au, shell 64 can include Ta or Nb, and outer layer 66 can include Pt—Ir, MP35N, or stainless steel.

In some embodiments, core 62 can include Ag, Au, Rh, Mo, alloy of Ta and Mo, Cu, Ir, Ta, or Ti, shell 64 can include stainless steel, Ta, MP35N, Pt, or Pt—Ir, and outer layer 66 can include Ag, Pt, Pt—Ir (5-30% Ir), Ta, Rh, Ti, stainless steel, MP35N, Pt—Rh, or Nb.

In one embodiment, core 62 includes Ir, shell 64 includes Ta, and outer layer 66 includes Pt.

In one embodiment, core 62 includes Mo, shell 64 includes Ta, and outer layer 66 includes Pt, Pt—Ir, or MP35N.

In one embodiment, core 62 includes Ag or Rh, shell 64 includes stainless steel, Ta, or MP35N, and outer layer includes Ag or Pt.

In some examples, core 62 is a composite formed as an embedded strand, such as will be discussed below (FIGS. 7, 9, and 10).

In some examples, a cross-sectional area of the core 62 is about 5% to about 50% of a cross-sectional area of the composite wire 60. In some examples, the cross-sectional area of the outer layer 66 is about 2% to about 20% of a cross-sectional area of the composite wire 60.

Figure 8:
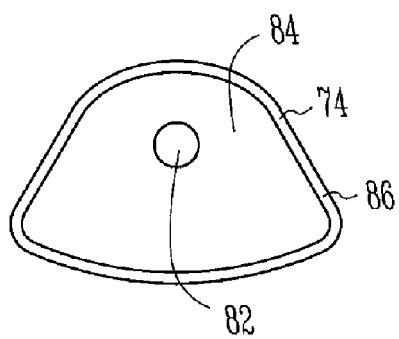
FIG. 8 shows a cross-section of a portion of the composite wire of FIG. 7.

FIG. 7 shows an example of an embedded strand wire 70 according to one embodiment. Wire 70 includes, for example, six strands 74 surrounding a core 72. FIG. 8 shows a portion of a strand 74, in accordance with one embodiment. In some examples, each strand is a homogenous strand and core 72 is homogenous. Materials usable for core 72 and strands 74 include those discussed above for the core and shell, respectively, of bi-layer wire 50 (FIG. 5). In some embodiments, core 72 includes Ag or Au.

In some examples, strands 74 are composite wires having a bi-layer structure (such as discussed above for composite wire 50) or a tri-layer structure including composite materials discussed above for tri-layer composite wire 60. For example, strand 74 can include a core 82, a shell or first layer 84, and an outer layer 86. The materials for these layers can be chosen from the materials discussed above for composite wire 60 (FIG. 6). In one embodiment, core 82 includes Ag or Rh, first layer 84 includes Ta, stainless steel, or MP35N, or combinations thereof, and outer layer 86 includes Ag.

Referring again to FIGS. 5 and 6, in some embodiments, core 52 of wire 50 or core 62 of wire 60 can include an embedded strand composite wire 70 of FIG. 7. For example, wire 60 can include shell 64 around an embedded strand core 62; the shell 64 can include stainless steel, Ta, MP35N, or Pt—Ir. Outer layer 66 can include Ag, Pt, Pt—Ir, Ta, Rh, Ti, or Nb.

FIG. 9 shows a composite wire 90, in accordance with one embodiment. Wire 90 includes a plurality of filaments 92 within an embedding matrix 94.

In some embodiments, wire 90 includes an Ag or Au matrix 94 and a plurality of peripheral filaments 92 including Ta or stainless steel. Wire 90 can be formed by cold drawing, for example.

In some examples, each of the plurality of filaments 92 includes a composite structure of two or more materials. In some embodiments, each filament 92 can be a composite wire such as any wires discussed above in FIG. 5, 6, or 7. For example, wire 90 can include an Ag embedding matrix 94 and a plurality of filaments 92. Each filament 92 can include a filament core including Ag or Rh and a shell around the filament core including Ta, stainless steel, or MP35N, and an outer layer around the shell including Ag, or other material.

In one embodiment, embedding matrix 94 can include Ag, Rh, or Au and filaments 92 can include stainless steel (316L SS, F138ASTM or F1314 ASTM w/ or w/o Nitrogen), a cobalt alloy such as MP35N, Ta, and Mo.

In some embodiments, embedding matrix 94 can include Rh or Au and filaments 92 can include stainless steel (316L SS, F138ASTM or F1314 ASTM w/ or w/o Nitrogen), cobalt alloy, Ta, or Mo.

In some embodiments, embedding matrix 94 can include Ag, Rh, and Au and filaments 92 can include a cobalt alloy, Ta, or Mo.

In some embodiments, there are six or more filaments 92 embedded in the matrix 94. In various embodiments a volume fraction of the matrix 94 is 15% to 40% of a total volume of the composite wire 90.

FIG. 10 shows a composite wire 100, in accordance with one embodiment. Wire 100 is an embedded strand having six outer strands 102 around a core 104. In this example, each of strands 102 includes an embedded matrix 106 and a plurality of filaments 108. Each of strands 102 can be formed of the material discussed for FIG. 9. In some examples, an outer layer can be positioned over the outer surface of wire 100. In other words, wire 100 can be used as a core wire for the composite wires of FIG. 5 or 6.

Figure 11:
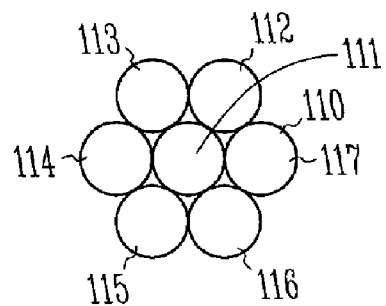
FIG. 11 shows a cross-section of a cable according to at least one embodiment.

FIG. 11 shows a cross-section of a cable 110 configured according to one embodiment. Cable 110 includes seven strands 111-117 in a 1×7 configuration. Strands 111-117 can be any of the composite wires discussed above. Strands 112-117 are twisted around a central strand 111.

Figure 12:
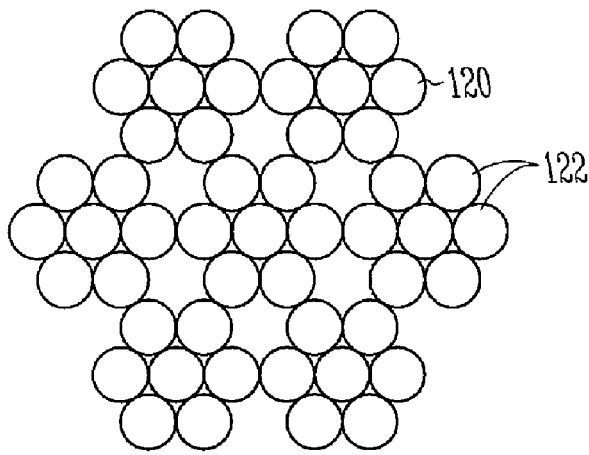
FIG. 12 shows a cross-section of a cable according to at least one embodiment.

FIG. 12 shows a cross-section of a cable 120 configured according to one embodiment. Cable 120 includes 49 strands 122 in a 7×7 configuration. The strands can be any of the composite wires discussed above. In this example, each group of seven strands are formed as the 1×7 cable of FIG. 11, then the seven groups are formed into the 7×7 configuration.

Figure 13:
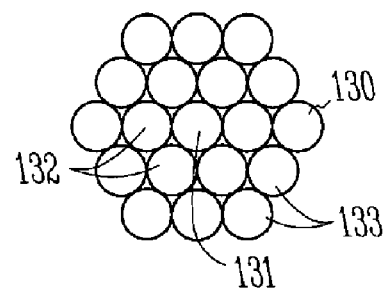
FIG. 13 shows a cross-section of a cable according to at least one embodiment.

FIG. 13 shows a cross-section of a cable 130 according to one embodiment. Cable 130 includes 19 strands in a 1×19 configuration. The strands can be any of the strands discussed above. In one embodiment, the core strand 131 can have a larger diameter than the second layers strands 132, which can have a larger diameter than the outer layer of strands 133.

One or more embodiments discussed above can be designed to optimize certain parameters during manufacture and use of the lead. For example, the material of the composite wire needs to be compatible with how the composite wire is going to be joined to the electrode (crimp, weld, laser weld, etc.). Thus, depending on the joining technique, different materials are chosen. Also, depending on the overall design of the lead, other materials can be chosen. For example, if the lead includes a lumen for over-the-wire delivery, then the conductor can be in contact with blood and the composite will need to have a certain acceptable level of corrosion resistance. Also, electrical resistance plays a role in choosing materials. Strength and flex fatigue are other factors. All these factors need to be considered in choosing the material for the composite wire.

By choosing a combination of materials that is appropriate for the desired design trade-offs, it is typically possible to reduce the diameter of the conductor cable relative to present designs and/or facilitate welding, crimping, or lead assembly. Thus, by way of example, gold or iridium can be selected for a core section of a composite wire since they have relatively low electrical resistance. Then a shell around that core can be constructed of a material such as Ta, MP35N, or Nb since these materials provide relatively good strength and resistance to deformation. In certain examples, an outer layer can be placed around the shell including material such as platinum or Pt—Ir, which provide a relatively good welding connection between the conductor and the electrode, for example.

It is understood that the above description is intended to be illustrative, and not restrictive. Many other embodiments will be apparent to those of skill in the art upon reviewing the above description. The scope of the invention should, therefore, be determined with reference to the appended claims, along with the full scope of equivalents to which such claims are entitled.

What is claimed is:

1. A composite wire comprising:
    an embedded strand wire including an Ag embedding matrix and a plurality of filaments including Ta within the matrix; and
    a shell around the embedding matrix including a material chosen from the group consisting of Ta, Pt, and Pt—Ir and combinations thereof.

2. The composite wire of claim 1, wherein the plurality of filaments includes six or more filaments.

3. The composite wire of claim 1, wherein a volume fraction of the matrix is 15% to 40% of a total volume of the composite wire.

4. The composite wire of claim 1, wherein the shell consists of Pt—Ir.

5. The composite wire of claim 1, wherein the shell consists of Pt.

6. The composite wire of claim 1, wherein the shell consists of Ta.

7. The composite wire of claim 1, wherein each of the filaments further includes Ag.

8. The composite wire of claim 1, wherein each of the filaments further includes Rh.

9. The composite wire of claim 1, wherein each of the filaments includes a bi-layer structure including a Ta core and a shell around the core including a material chosen from the group consisting of Pt—Ir, Pt, Nb, cobalt alloy, stainless steel, and combinations thereof.

10. The composite wire of claim 1, wherein each of the filaments includes a bi-layer structure having a core including a material chosen from the group consisting of Ag, Au, and Mo, and combinations thereof, and a shell around the core including Ta.

11. The composite wire of claim 1, wherein each of the filaments includes a bi-layer structure having a core including Ir and a shell around the core including Ta.

12. An implantable lead comprising:
    an implantable lead body extending from a distal end to a proximal end;
    a conductor disposed within the lead body, the conductor including a composite wire comprising:
    an embedded strand wire including an Ag embedding matrix and a plurality of filaments including Ta within the matrix; and
    a shell around the embedding matrix including a material chosen from the group consisting of Ta, Pt, and Pt—Ir and combinations thereof.

13. The implantable lead of claim 12, wherein the plurality of filaments includes six or more filaments.

14. The implantable lead of claim 12 wherein a volume fraction of the matrix is 15% to 40% of a total volume of the composite wire.

15. The implantable lead of claim 12, wherein wherein the shell consists of Pt—Ir.

16. The composite wire of claim 12, wherein the shell consists of Pt.

17. The composite wire of claim 12, wherein the shell consists of Ta.

18. The composite wire of claim 12, wherein each of the filaments further includes Ag.

19. The composite wire of claim 12, wherein each of the filaments further includes Rh.

20. The composite wire of claim 12, wherein each of the filaments includes a bi-layer structure including a Ta core and a shell around the core including a material chosen from the group consisting of Pt—Ir, Pt, Nb, cobalt alloy, stainless steel, and combinations thereof.

21. The composite wire of claim 12, wherein each of the filaments includes a bi-layer structure having a core including a material chosen from the group consisting of Ag, Au, and Mo, and combinations thereof, and a shell around the core including Ta.

22. The composite wire of claim 12, wherein each of the filaments includes a bi-layer structure having a core including Ir and a shell around the core including Ta.

* * * * *

UNITED STATES PATENT AND TRADEMARK OFFICE
CERTIFICATE OF CORRECTION

PATENT NO.      : 7,612,291 B2
APPLICATION NO. : 11/558147
DATED           : November 3, 2009
INVENTOR(S)     : Stuart R. Chastain et al.

It is certified that error appears in the above-identified patent and that said Letters Patent is hereby corrected as shown below:

In column 7, line 1, in Claim 15, after "wherein" delete "wherein".

Signed and Sealed this

Twelfth Day of January, 2010

David J. Kappos
*Director of the United States Patent and Trademark Office*